(12) United States Patent
Zakhary

(10) Patent No.: US 10,123,857 B2
(45) Date of Patent: Nov. 13, 2018

(54) DENTAL EXPANSION ASSEMBLY

(71) Applicant: Ibrahim Zakhary, Troy, MI (US)

(72) Inventor: Ibrahim Zakhary, Troy, MI (US)

( * ) Notice: Subject to any disclaimer, the term of this patent is extended or adjusted under 35 U.S.C. 154(b) by 60 days.

(21) Appl. No.: 14/875,722

(22) Filed: Oct. 6, 2015

(65) Prior Publication Data

US 2016/0100901 A1    Apr. 14, 2016

Related U.S. Application Data

(60) Provisional application No. 62/071,877, filed on Oct. 6, 2014.

(51) Int. Cl.
| | |
|---|---|
| *A61C 8/00* | (2006.01) |
| *A61B 19/00* | (2006.01) |
| *A61C 8/02* | (2006.01) |
| *A61B 90/00* | (2016.01) |

(52) U.S. Cl.
CPC .......... *A61C 8/0089* (2013.01); *A61B 19/24* (2013.01); *A61B 90/02* (2016.02); *A61C 8/0006* (2013.01)

(58) Field of Classification Search
CPC .......... A61B 2010/0208; A61B 1/0053; A61B 17/02; A61B 90/02; A61B 19/24; A61C 8/0089; A61C 8/006; A61C 8/0092; A61F 2002/285
USPC ................................................ 433/176, 173
See application file for complete search history.

(56) References Cited

U.S. PATENT DOCUMENTS

| | | | | |
|---|---|---|---|---|
| 153,009 | A * | 7/1874 | Nesbitt | B27L 7/06 111/99 |
| 819,136 | A * | 5/1906 | Herman | A61C 5/88 433/149 |
| 1,534,066 | A * | 4/1925 | Larkey | B25B 27/062 29/261 |
| 3,108,883 | A * | 10/1963 | Goeser | B26D 7/10 426/518 |
| 3,579,829 | A * | 5/1971 | Sampson | A61C 8/0089 433/158 |

(Continued)

FOREIGN PATENT DOCUMENTS

| | | | | |
|---|---|---|---|---|
| EP | 2076206 B1 | * | 8/2016 | ........... A61C 8/0033 |
| WO | WO 2006017221 A2 | * | 2/2006 | ........... A61C 1/0007 |

OTHER PUBLICATIONS

Aparicio, C. and Jensen, O.T. ((2001). Alveolar ridge widening by distraction osteogenesis: A case report. Prac Proced Aesthet Dent 2001; 13(8):663-668.

(Continued)

*Primary Examiner* — Nicholas Lucchesi
*Assistant Examiner* — Shannel Wright
(74) *Attorney, Agent, or Firm* — Carlson, Gaskey & Olds, P.C.

(57) ABSTRACT

An assembly for expansion of tissue according to an example of the present disclosure includes, among other things, a body extending between proximal and distal ends. The body includes a head portion at the proximal end, and at least two arm portions extending between the head portion and the distal end to define an actuation cavity. Each of the at least two arm portions are configured to abut tissue. An actuation member is received in the actuation cavity. The actuation member is moveable to vary a distance between the at least two arm portions at the distal end.

20 Claims, 6 Drawing Sheets

(56) References Cited

U.S. PATENT DOCUMENTS

| | | | | |
|---|---|---|---|---|
| 3,750,652 A * | 8/1973 | Sherwin | A61B 17/025 | 600/217 |
| 5,562,447 A * | 10/1996 | Moy | A61C 8/0089 | 433/150 |
| 5,667,520 A * | 9/1997 | Bonutti | A61B 17/0218 | 600/204 |
| 5,716,325 A * | 2/1998 | Bonutti | A61B 17/0218 | 600/153 |
| 5,810,721 A * | 9/1998 | Mueller | A61B 17/0293 | 600/200 |
| 6,309,220 B1 * | 10/2001 | Gittleman | A61B 17/176 | 433/173 |
| 6,471,515 B2 * | 10/2002 | Feuer | A61B 17/30 | 433/162 |
| 7,025,592 B2 * | 4/2006 | Corti | A61B 17/666 | 433/153 |
| 7,396,232 B2 * | 7/2008 | Fromovich | A61B 90/02 | 433/173 |
| 7,600,325 B2 * | 10/2009 | Zipplies | A61C 8/0089 | 33/512 |
| 7,874,839 B2 * | 1/2011 | Bouneff | A61C 1/0007 | 433/118 |
| 8,206,151 B2 * | 6/2012 | McDonald | A61C 5/127 | 433/148 |
| 8,298,139 B2 * | 10/2012 | Hamada | A61B 17/02 | 600/233 |
| 8,377,070 B2 * | 2/2013 | Gauthier | A61B 17/025 | 606/90 |
| 8,647,120 B2 * | 2/2014 | Marteney | A61C 3/00 | 433/148 |
| 8,845,648 B2 * | 9/2014 | Guzman | A61B 17/1635 | 606/280 |
| 9,107,719 B2 * | 8/2015 | Gauthier | A61B 17/025 | |
| 9,351,814 B2 * | 5/2016 | Mahl | A61C 8/00 | |
| 9,801,734 B1 * | 10/2017 | Stein | A61F 2/447 | |
| 2003/0143513 A1 * | 7/2003 | Flanagan | A61C 8/0089 | 433/141 |
| 2003/0186194 A1 * | 10/2003 | Corti | A61B 17/666 | 433/153 |
| 2005/0177159 A1 * | 8/2005 | Guzman | A61B 17/1635 | 606/67 |
| 2007/0100366 A1 * | 5/2007 | Dziedzic | A61B 17/02 | 606/191 |
| 2010/0304328 A1 * | 12/2010 | Schweizer | A61C 8/0089 | 433/141 |
| 2011/0269103 A1 * | 11/2011 | Shimko | A61C 8/0033 | 433/173 |
| 2011/0306981 A1 * | 12/2011 | Wang | A61C 8/0089 | 606/83 |
| 2012/0136364 A1 * | 5/2012 | Teramoto | A61C 1/084 | 606/102 |
| 2014/0120497 A1 * | 5/2014 | Marteney | A61C 5/127 | 433/149 |
| 2014/0244016 A1 * | 8/2014 | Stumpel | A61C 1/084 | 700/98 |
| 2016/0213500 A1 * | 7/2016 | Beger | A61B 17/025 | |

OTHER PUBLICATIONS

Chiapasco, M., Ferrini, F., Casentini, P., Accardi, S., and Zaniboni, M. (2005). Dental implants placed in expanded narrow edentulous ridges with the Extension Crest devise. A 1-3 year multicenter follow-up study. Clin. Oral Imp. Res. 17, 2006; 265-272.

Laster, Z., Rachmiel, A. and Jensen, O.T. (2005). Alveolar width distraction osteogenesis for early implant placement. American Association of Oral and Maxillofacial Surgeons. p. 1724-1730.

Distraction devices overview: Sophisticated products in OMF surgery. KLS Martin Group publication. 2010.

* cited by examiner

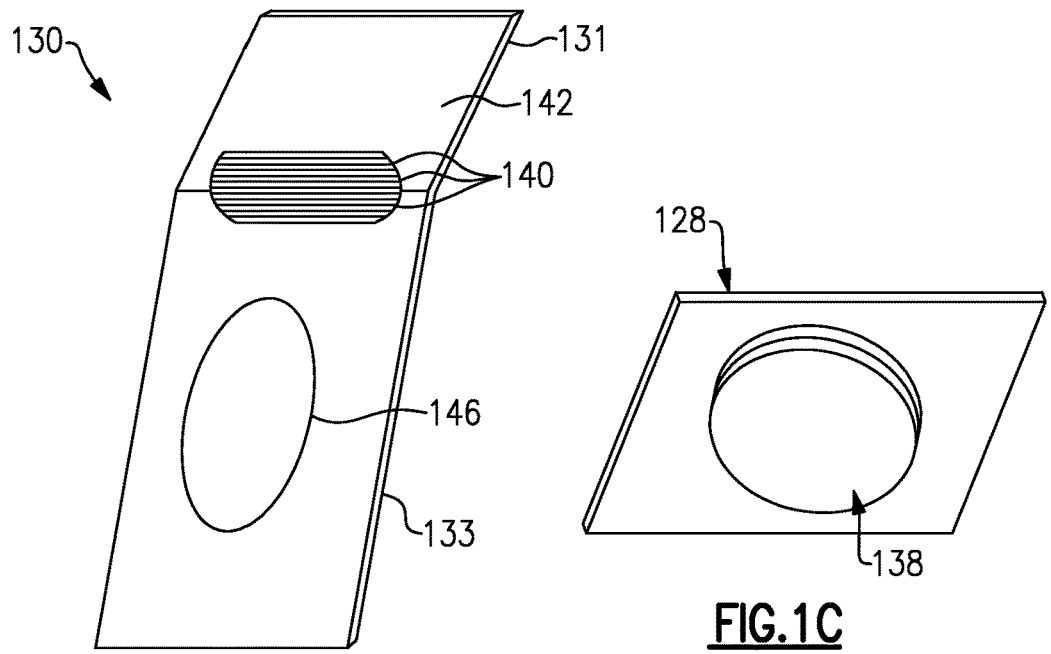
FIG.1B
FIG.1C
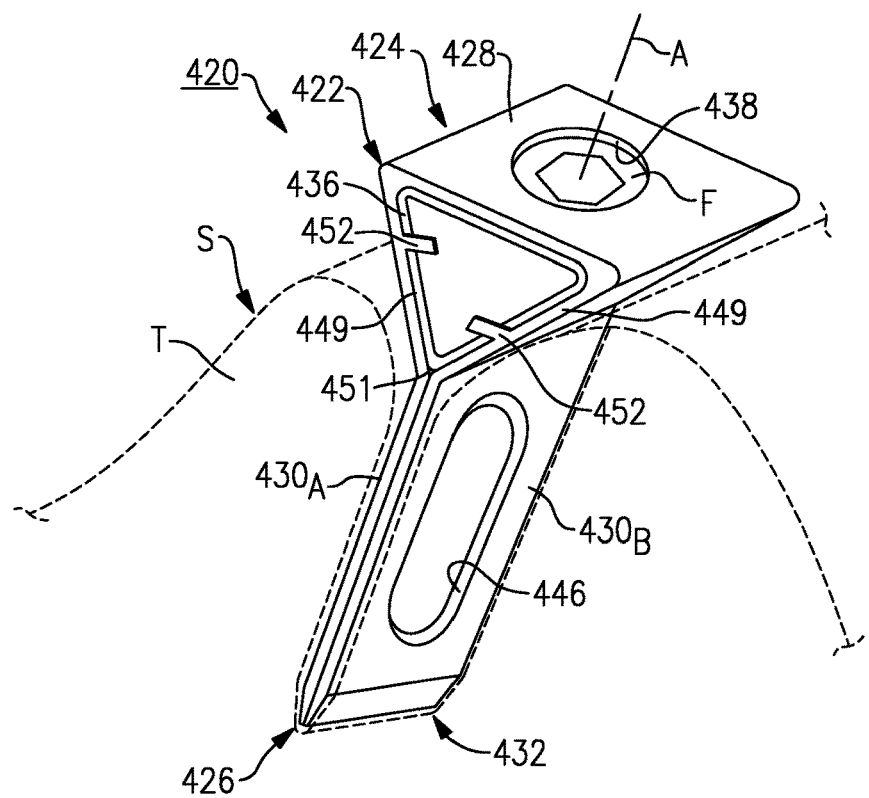
FIG.5A

DENTAL EXPANSION ASSEMBLY

CROSS-REFERENCE TO RELATED APPLICATION

This application claims the benefit of U.S. Provisional Patent Application Ser. No. 62/071,877, filed on Oct. 6, 2014.

BACKGROUND

The present disclosure generally relates to dental instrumentation and procedures, and more particularly to an assembly for expansion of tissue.

Tooth extraction is known a dental procedure which may be performed prior to placement of a surgical implant in a patient. In some situations, the extraction procedure is performed at the surgical site several months or years before the implantation procedure occurs. During this period of time, the patient may experience horizontal and vertical bone tissue loss at the surgical site, such as along the alveolar ridge. Accordingly, the dental practitioner may perform a procedure to increase a width of the alveolar ridge prior to implant placement.

SUMMARY

An assembly for expansion of tissue according to an example of the present disclosure includes a body extending between proximal and distal ends. The body includes a head portion at the proximal end, and at least two arm portions extending between the head portion and the distal end to define an actuation cavity. Each of the at least two arm portions are configured to abut tissue. An actuation member is received in the actuation cavity. The actuation member is moveable to vary a distance between the at least two arm portions at the distal end.

In a further embodiment of any of the forgoing embodiments, the actuation member is a fastener configured to be received in an aperture defined by the head portion.

In a further embodiment of any of the forgoing embodiments, the head portion defines an aperture configured to receive a dental instrument.

In a further embodiment of any of the forgoing embodiments, the actuation member includes side walls joined at an apex, a projection of the apex extending towards the distal end.

In a further embodiment of any of the forgoing embodiments, a cross-section of the actuation member defines a triangular geometry.

In a further embodiment of any of the forgoing embodiments, each of the at least two arm portions includes a first section coupled to the head portion and a second section terminating at the distal end. The first section slopes inwardly from the head portion to bound the actuation cavity.

In a further embodiment of any of the forgoing embodiments, the second section defines an aperture extending inwardly from outer surfaces of the second section, the aperture configured to receive tissue.

In a further embodiment of any of the forgoing embodiments, the aperture is one or more elongated slots.

In a further embodiment of any of the forgoing embodiments, the at least two arm portions taper at the distal end to define an engagement region. The engagement region configured to pierce tissue.

In a further embodiment of any of the forgoing embodiments, each of the at least two arm portions defines one or more forks configured to interlock with an adjacent fork of another one of the at least two arm portions.

In a further embodiment of any of the forgoing embodiments, the actuation member is moveable along a longitudinal axis extending between the proximal and distal ends, and each of the at least two arm portions is pivotable relative to the longitudinal axis.

In a further embodiment of any of the forgoing embodiments, the at least two arm portions are integrally formed with the head portion such that surfaces of the at least two arm portions load against each other when the actuation member is located in a first position.

An assembly for expansion of tissue according to an example of the present disclosure includes a head portion at a proximal end, and a pair of elongated arm portions extending between the head portion and a distal end. Each of the pair of arm portions is configured to abut tissue. A wedge shaped actuation member is moveable between the proximal and distal ends to cause each of the pair of arm portions to pivot relative to the head portion, thereby spacing apart the pair of arm portions at the distal end.

In a further embodiment of any of the forgoing embodiments, each of the pair of arm portions slopes inwardly from the head portion to define an actuation cavity. The actuation member is trapped in the actuation cavity.

In a further embodiment of any of the forgoing embodiments, the pair of arm portions are integrally formed with the head portion such that the pair of arm portions abut against surfaces of the actuation member.

In a further embodiment of any of the forgoing embodiments, one or more apertures are defined in a thickness of at least one of the arm portions. The one or more apertures are dimensioned to receive tissue.

A method of expanding bone tissue according to an example of the present disclosure includes, providing the assembly as recited in claim 1, positioning the distal end of the assembly against bone tissue, engaging the head portion to cause the distal end to move a distance through the bone tissue, and moving the actuation member relative to the at least two arm portions to cause the bone tissue to separate.

A further embodiment of any of the foregoing embodiments includes receiving bone tissue within an aperture defined in a thickness of at least one of the arm portions subsequent to the step of moving the actuation member.

A further embodiment of any of the foregoing embodiments includes moving the actuation member to cause the at least two arm portions to abut against each other, and removing the assembly from the bone tissue.

A further embodiment of any of the foregoing embodiments includes guiding a device through the head portion and between the arm portions to engage bone tissue.

The various features and advantages of this disclosure will become apparent to those skilled in the art from the following detailed description. The drawings that accompany the detailed description can be briefly described as follows.

BRIEF DESCRIPTION OF THE DRAWINGS

FIG. 1B illustrates an arm portion of the assembly of FIG. 1A.

FIG. 1C illustrates a head portion of the assembly of FIG. 1A.

FIG. 5A illustrates a perspective view of an assembly for expansion of tissue according to a fourth example, the assembly situated in tissue and in a deactivated condition.

DETAILED DESCRIPTION

Figure 1A:
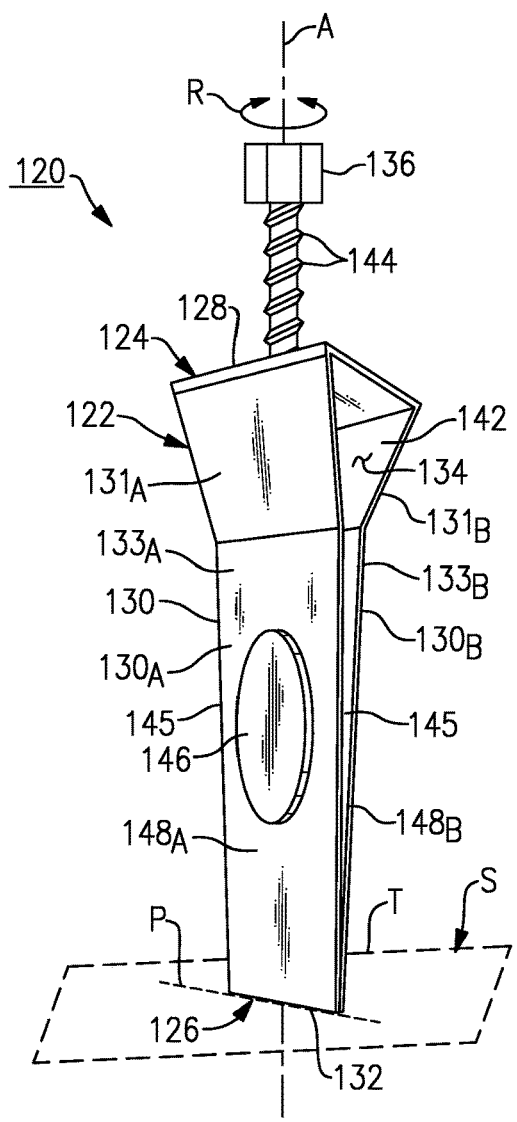
FIG. 1A is a perspective view of an assembly for dental expansion in a deactivated condition.

FIGS. 1A to 1C and 2 illustrate an assembly 120 for expansion of tissue, according to an example. The assembly 120 can be utilized to separate or expand bone tissue, such as along a jaw ridge, for example. The assembly 120 can also be utilized to promote growth of bone tissue, for example, by situating the assembly 120 at the surgical site for a period of time, thereby increasing tissue thickness at the surgical site and reducing the need for a bone tissue graft. Although the techniques described herein primarily refer to bone tissue along the jaw ridge, such as the alveolar ridge, the techniques described herein are not limited to such location and may be applied to other anatomical locations and medical or dental procedures. Additionally, although a particular component arrangement is disclosed in the illustrated embodiment, other arrangements will benefit herefrom. It should be understood that like reference numerals identify corresponding or similar elements throughout the several drawings.

The assembly 120 includes a body 122 extending along a longitudinal axis A between a proximal end 124 and a distal end 126. The body 122 includes a head portion 128 at the proximal end 124 and one or more arm portions 130 coupled to the head portion 128. In the illustrated example, the arm portions 130 include two elongated arm portions 130A, 130B extending between the head portion 128 and the distal end 126 in a direction generally parallel to the longitudinal axis A. The arm portions 130A, 130B can be dimensioned for expansion of bone tissue at the previous site of one or more teeth along the jaw ridge, for example.

Figure 2:
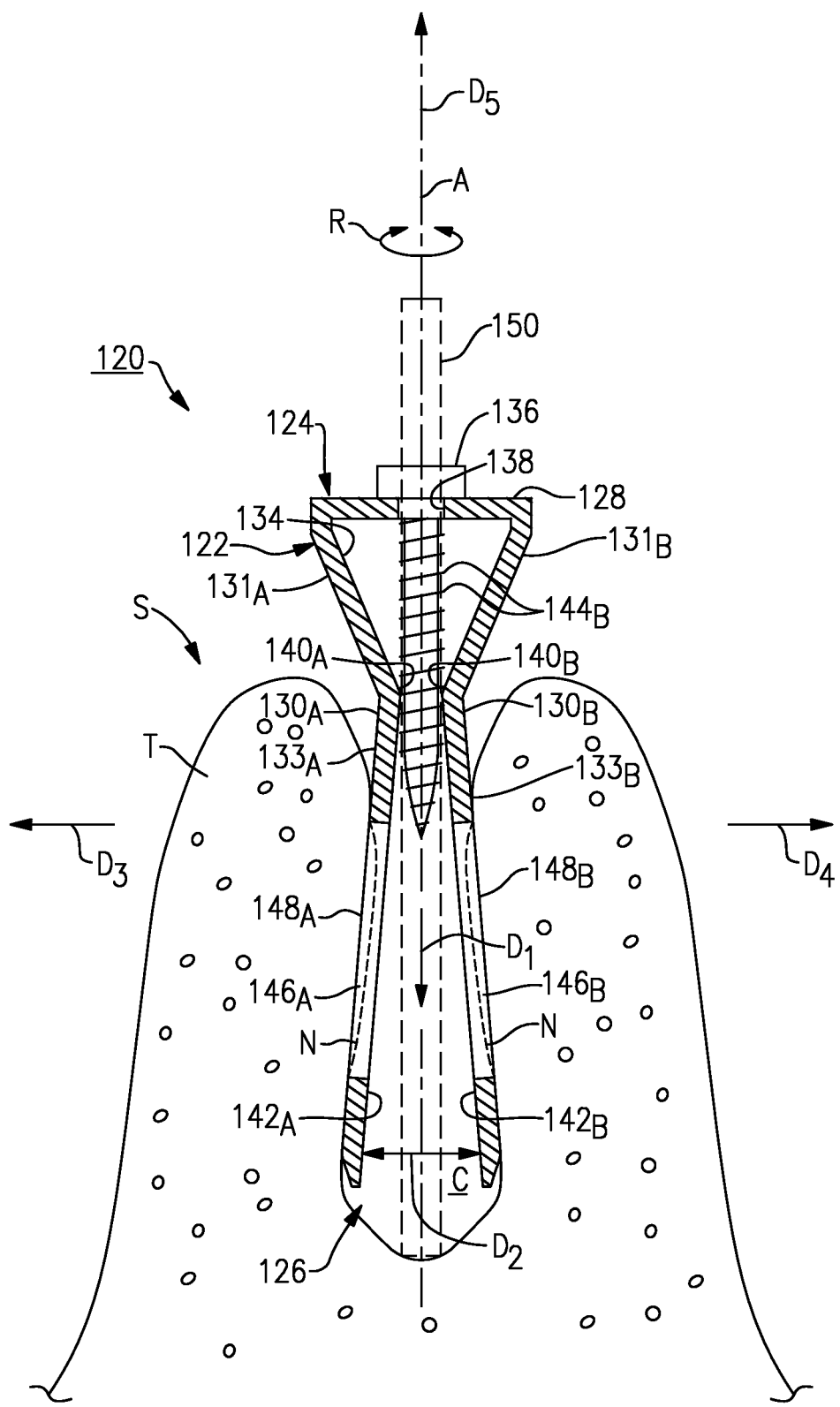
FIG. 2 schematically illustrates a cross sectional view of the assembly of FIG. 1A, the assembly situated in tissue and in an activated condition.

The arm portions 130A, 130B are configured to abut tissue T when in an installed or activated condition (FIG. 2). The arm portions 130A, 130B define an engagement region 132 at the distal end 126 operable to pierce tissue T, such as cortical bone tissue, for example. In the illustrated example, the arm portions 130A, 130B taper towards the distal end 126 to define the engagement region 132.

The head portion 128 and the arm portions 130A, 130B are arranged to define an actuation cavity 134. The arm portions 130A, 130B include first sections 131A, 131B coupled to the head portion 128 and second sections 133A, 133B terminating at the distal end 126. In the illustrated example, the first sections 131A, 131B slope inwardly from the head portion 128 to bound or otherwise define the actuation cavity 134.

An actuation member 136 is selectively received in the actuation cavity 134. The actuation member 136 is configured to abut against inner surfaces 142 of the arm portions 130A, 130B. The actuation member 136 is configured to cause the assembly 120 to change between deactivated and activated conditions, as discussed in detail below.

In the illustrated example, the actuation member 136 is a fastener, such as a threaded screw, selectively received in an aperture 138 (FIG. 1C) defined in the head portion 128. The actuation member 136 is configured to engage one or more serrations 140 (FIG. 1B) defined along inner surfaces 142 of the arm portions 130A, 130B. The serrations 140 are configured to engage and guide corresponding threads 144 of the actuation member 136 during rotation of the actuation member 136 in a direction R about the longitudinal axis A such that the actuation member 136 translates along the longitudinal axis A.

In some examples, the arm portions 130A, 130B are integrally formed with the head portion 128 such that inner surfaces 142 of the arm portions 130A, 130B load against each other when the actuation member 136 is located in a deactivated (or first) position. In another example, the arm portions 130A, 130B are discrete components mechanically coupled to the head portion 128, such as by a hinge joint or the like. The arrangement of the arm portions 130A, 130B can reduce stress concentration of the adjacent tissue T near the proximal end 124, by causing the arm portions 130A, 130B to pivot near the proximal end 124 and separate at the distal end 126.

Figure 3:
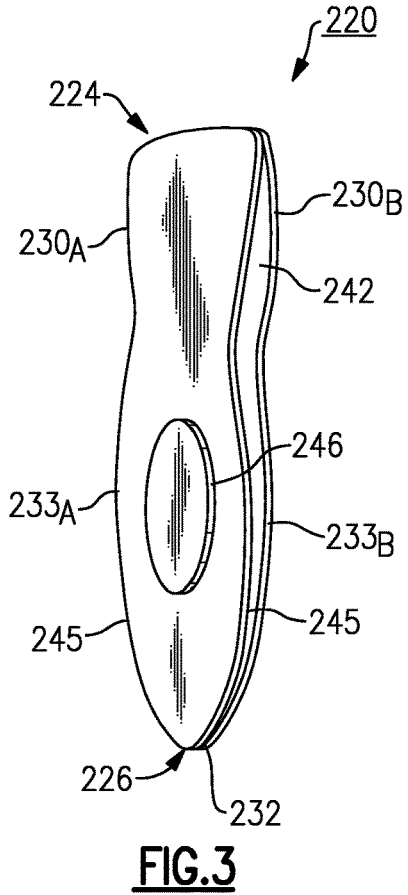
FIG. 3 illustrates a perspective view of an assembly for expansion of tissue according to a second example.

In the illustrated example, the arm portions 130A, 130B have a substantially planar geometry along the outer surfaces 148A, 148B. In another example, sidewalls 245 of the arm portions 230A, 230B taper towards distal end 226 to define a pointed engagement region 232, as shown in FIG. 3. The pointed geometry of the engagement region 232 may be suitable for piercing relatively hard or dense tissue, such as D1 or D2 bone tissue, for example. The arm portions 230A, 230B can be directly coupled to each other at proximal end 224 such that a separate head portion is omitted.

Referring back to FIGS. 1A to 1C and 2, the second sections 133A, 133B of arm portions 130A, 130B can define one or more apertures 146 defined in a thickness of the arm portions 130A, 130B. In the illustrated example, two apertures 146A are spaced a distance from sidewalls 145 and extend inwardly from outer surfaces 148A, 148B of the second sections 133A, 133B. Each aperture 146 is configured to receive an ingrowth of tissue N (FIG. 2), such as bone tissue, when the arm portions 130A, 130B are situated in a surgical site S for a desired period of time. The arrangement of each aperture 146 can promote ingrowth of tissue N within the aperture 146, thereby increasing an overall thickness and strength of the surgical site S. In the illustrated example, each aperture 145 has a generally elliptical geometry. In another example, the apertures are elongated slots (indicated at 446 in FIG. 5B).

Operation of the assembly 120 is as follows. The assembly 120 is moveable between a deactivated (or first) condition (FIG. 1A) and an activated (or second) condition (FIG. 2) to cause expansion of tissue T at the surgical site S. During operation, a practitioner or operator can create an incision and trough P (FIG. 1A) at the surgical site S for situating the engagement region 132 in a desired location and/or orientation. The practitioner positions the distal end 126 of the assembly 120 against tissue T.

Referring to FIG. 2, the practitioner engages the head portion 128 with an instrument, such as a mallet, to drive or otherwise move the distal end 126 of the assembly 120 in a direction D1 through the tissue T. Driving the distal end 126 of the assembly 120 causes the tissue T, such as cortical bone tissue at the alveolar ridge, to separate or split apart by a width corresponding to the arm portions 130A, 130B.

The practitioner engages the actuation member 136, such as by rotating the actuation member 136 in the direction R about the longitudinal axis A, to cause the actuation member 136 to move relative to the arm portions 130A, 130B. Movement of the actuation member 136 varies a distance D2 between the arm portions 130A, 130B at the distal end 126, thereby causing adjacent tissue T to further separate or split apart in directions D3, D4.

The practitioner may desire to position the assembly 120 at the surgical site S for a period time such that apertures 146A, 146B receive an ingrowth of new tissue N (schematically shown in dashed lines in FIG. 2). The actuation member 136 can be adjusted to increase and/or decrease the distance D2 between the arm portions 130A, 130B. To deactivate the assembly 120, the practitioner can engage the actuation member 136, thereby translating the actuation member 136 along the longitudinal axis A and causing the arm portions 130A, 130B to abut against each other (FIG. 1A).

In some examples, the assembly 120 is configured as a guide or access portal. For example, the actuation member 136 can be removed from the aperture 138 of head portion 128 to provide access to the cavity 134. The aperture 138 can be configured to receive an instrument or device 150 (shown schematically in dashed lines in FIG. 2). In some examples, the device 150 is a drill bit, reamer, or cannulated shaft dimensioned to selectively extend past the distal end 126 of the assembly 120. In another example, the device is a surgical implant. The practitioner can guide the device 150 through the head portion 128 and between the arm portions 130A, 130B to engage tissue T at the surgical site S, such as bone tissue surrounding a cavity C (FIG. 2) formed by expansion of the arm portions 130A, 130B. The practitioner may move the assembly 120 in a direction D5 to remove the assembly 120 from the surgical site S.

Figure 4:
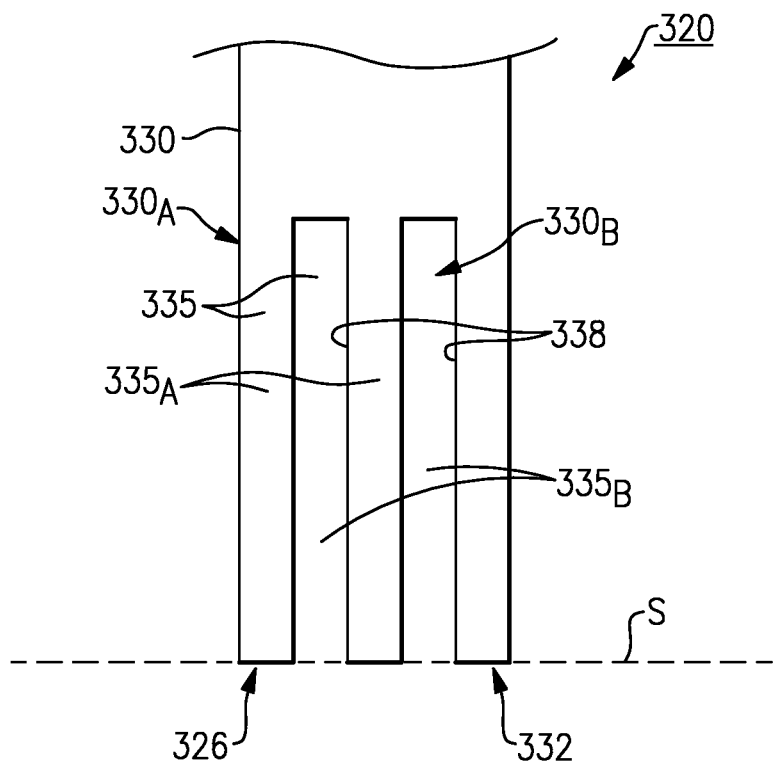
FIG. 4 illustrates a side view of arm portions of an assembly for expansion of tissue according to a third example.

In the example of FIG. 4, arm portions 330 define one or more apertures 338 between one or more forks 335 to promote ingrowth of tissue. In the illustrated example, arm portion 330A defines one or more forks 335A, and arm portion 330B defines one or more forks 335B. Forks 335A of arm portion 330A are configured to interlock with adjacent forks 335B of arm portion 330B such that the forks 335A, 335B define a substantially continuous engagement region 332 for abutting against an adjacent surface S. In alternative examples, the forks 335A, 335B abut against each other. The forks 335A, 335B facilitate piercing of the distal end 326 through tissue at the surface S, and separation of forks 335A, 335B to promote ingrowth of tissue between the forks 335A, 335B. The forks 335A, 335B facilitate removal of the distal end 326 from the surgical site while reducing disturbance of tissue between the forks 335A, 335B, such as situations in which the forks 335A, 335B are not fully positioned in a deactivated condition.

Figure 5B:
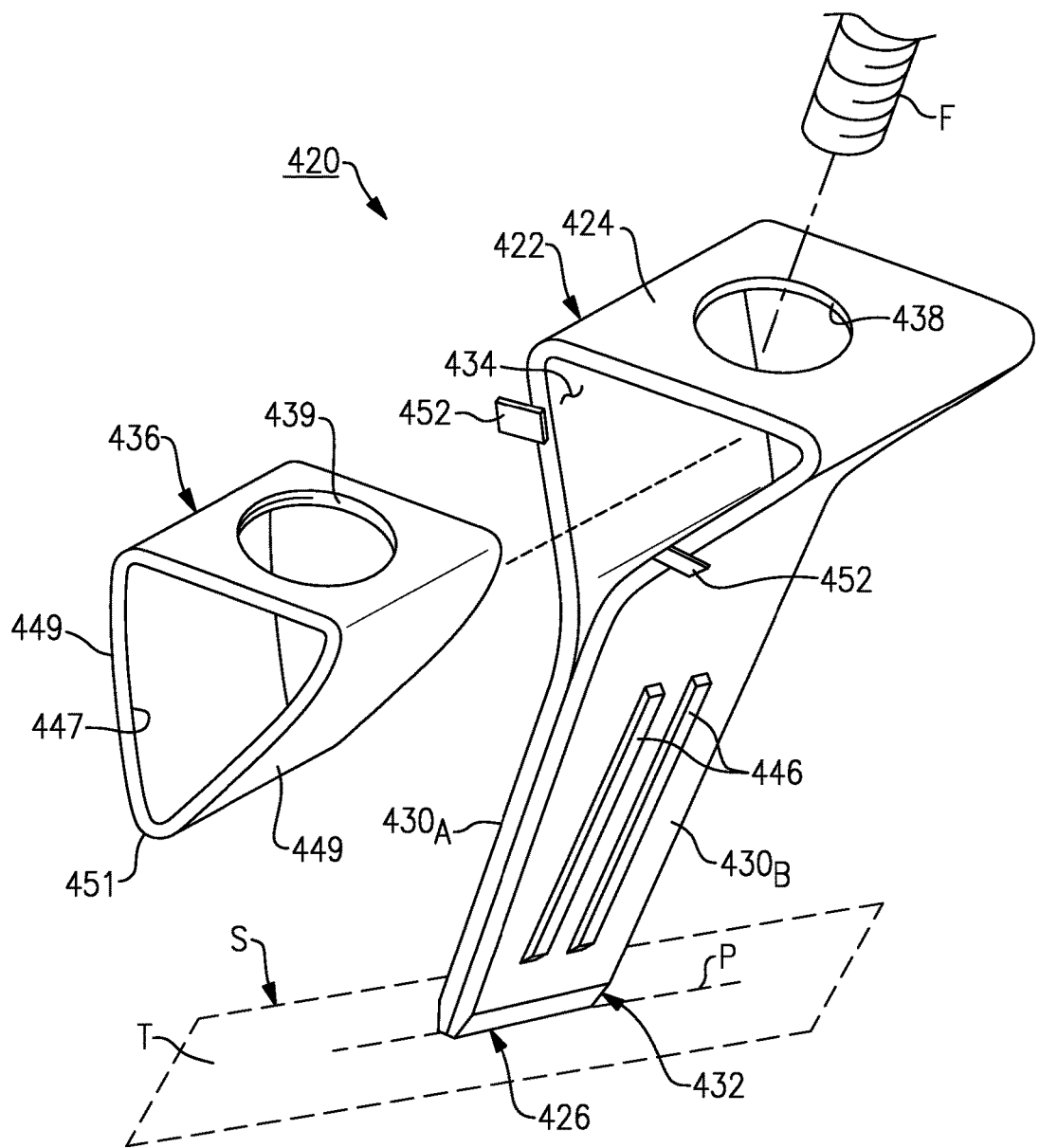
FIG. 5B illustrates an exploded view of the assembly of FIG. 5A.
Figure 6:
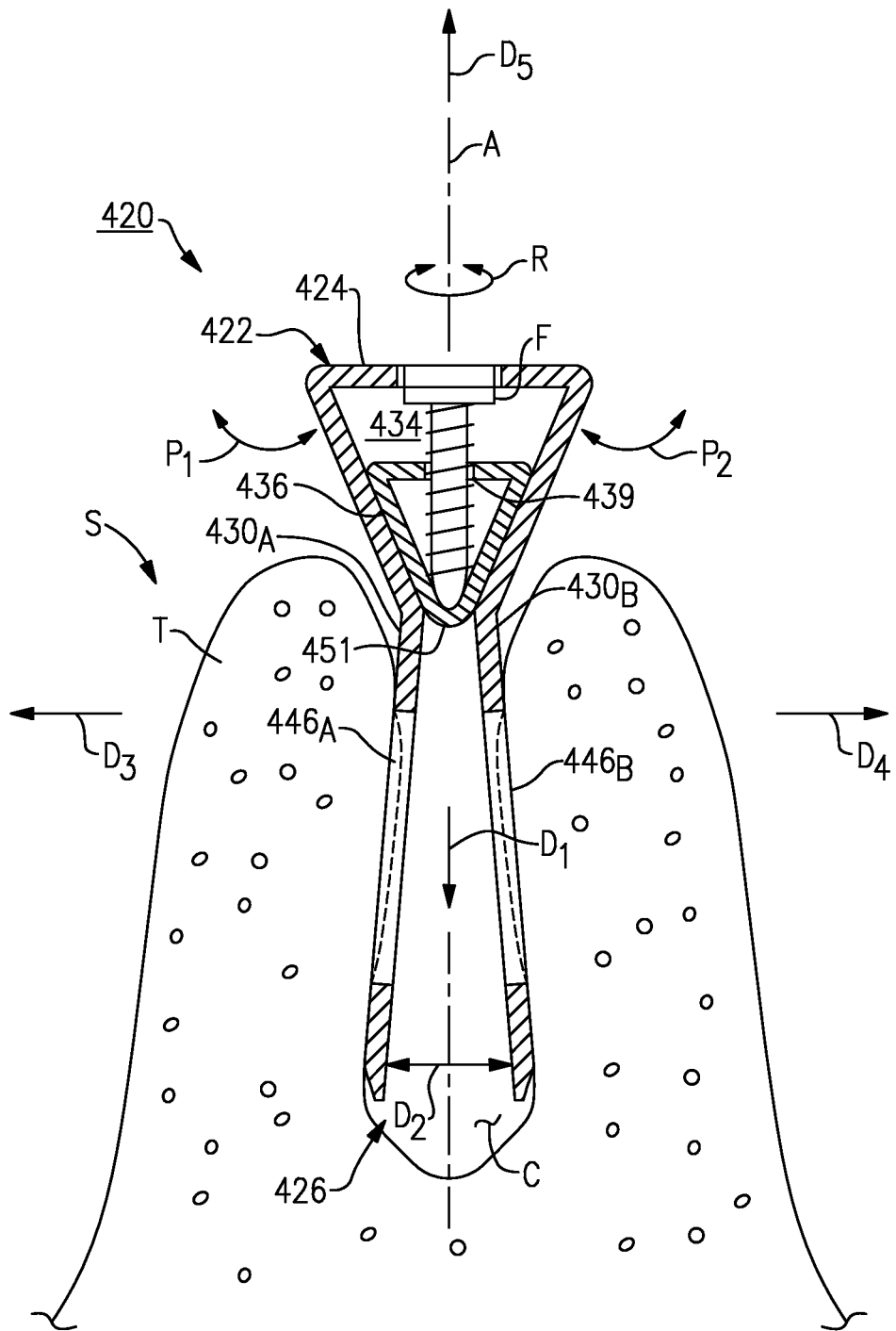
FIG. 6 schematically illustrates a cross sectional view of the assembly of FIG. 5A, the assembly situated in tissue and in an activated condition.

FIGS. 5A to 5B and 6 illustrate an assembly 420 for expansion of tissue according to a fourth example. FIG. 5A illustrates the assembly 420 situated within tissue T at a surgical site S and in a deactivated condition. FIG. 5B is an exploded view of the assembly 420. FIG. 6 illustrates the assembly 420 in an activated condition such that adjacent tissue T is separated at the surgical site S to define a cavity C.

The assembly 420 includes a wedge shaped actuation member 436. The actuation member 436 includes side walls 449 joined at an apex 451. The actuation member 436 can be situated in actuation cavity 434 such that a projection of the apex 451 extends towards the distal end 426. In the illustrated example, a cross-section of the actuation member 436 defines a generally triangular geometry. In an alternative example, the actuation member 436 is elongated along longitudinal axis A such that a cross-section of the actuation member 436 includes more than three sides.

The wedge shaped actuation member 436 is moveable along longitudinal axis A to cause arm portions 430A, 430B to pivot in directions P1, P2 (FIG. 6) relative to the longitudinal axis A and/or relative to head portion 428, thereby spacing apart the arm portions 430A, 430B at distal end 426. The actuation member 436 defines a hallow cavity 447 accessible by an aperture 439. In alternative examples, the actuation member 436 is substantially solid or encloses the hollow cavity 447.

The aperture 439 of the actuation member 436 can be aligned with aperture 438 of the head portion 428 to receive a fastener F, for example. The fastener F, such as a threaded screw having a hexagon socket, may be arranged to be substantially flush with adjacent surfaces of the head portion 428, thereby reducing the overall length of the assembly 420 and increasing mobility at the surgical site S. The aperture 439 can be threaded such that rotation of the fastener F causes the actuation member 436 to translate along longitudinal axis A. The wedge shaped actuation member 436 and fastener F can be dimensioned to define a predefined amount of expansion of the arm portions 430A, 430B for each full turn of the fastener F, which may be adjusted over a desired period of time. In alternative examples, a pin or another device is utilized to cause the actuation member 436 to translate along the longitudinal axis A and/or fix the actuation member 436 at a desired position.

The arm portions 430A, 430B slope inwardly from the head portion 428 to define an actuation cavity 434 such that the actuation member 436 is trapped in the actuation cavity 434 when installed therein. The arm portions 430A, 430B define an engagement region 432 at the distal end 426 operable to pierce tissue T. The assembly 420 can include one or more fixation members 452 extending from body 422, such as arm portions 430A, 430B, for example, configured to limit relative movement of the actuation member 436 within the actuation cavity 434. In the illustrated example, the fixation members 452 are one or more tabs which can be bent or oriented to a desired position to trap or otherwise retain the actuation member 436 in the actuation cavity 434.

The techniques described herein can be utilized to restore normal function, phonetics and facial dimensions or other esthetics of a patient, for example. The assemblies 120, 220, 320, 420 described herein can be utilized in an osteotme technique to widen a horizontally atrophied alveolar ridge, such as intraoperative expansion of relative soft D3 or D4 bone tissue, for example. The assemblies can also be utilized for distraction osteogenesis (DO) in the formation or regeneration of tissue, such as for expanding a width or thickness of relatively hard or dense D1 and D2 bone tissue along a jaw ridge. Components of the assemblies can be formed from surgical grade stainless steel or another suitable material.

Although the different examples have a specific component shown in the illustrations, embodiments of this disclosure are not limited to those particular combinations. It is possible to use some of the components or features from one of the examples in combination with features or components from another one of the examples. Although particular step sequences are shown, described, and claimed, it should be understood that steps may be performed in any order, separated or combined unless otherwise indicated and will still benefit from the present disclosure.

Furthermore, the foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

What is claimed is:

1. An assembly for expansion of tissue, comprising:
a body extending between proximal and distal ends, the body comprising:
   a head portion at the proximal end, and
   at least two arm portions extending between the head portion and the distal end to define an actuation cavity, each of the at least two arm portions tapering towards the distal end to define a pointed engagement region operable to abut and pierce tissue;
wherein each of the at least two arm portions includes a first section coupled to the head portion and a second section terminating at the distal end, the first section sloping inwardly from the head portion to bound the actuation cavity;
wherein each second section defines an aperture extending inwardly from outer surfaces of the second section, the aperture configured to receive tissue along a bone cavity defined in a jaw ridge; and
an actuation member received in the actuation cavity, the actuation member moveable along a longitudinal axis extending between the proximal and distal ends to vary a distance between the at least two arm portions at the distal end, thereby spacing apart terminal ends of the at least two arm portions at the distal end such that the actuation member is axially spaced apart from each aperture with respect to the longitudinal axis, and the aperture is axially spaced apart from the engagement region with respect to the longitudinal axis.

2. The assembly as recited in claim 1, wherein the actuation member is a fastener configured to be received in a head aperture defined by the head portion.

3. The assembly as recited in claim 1, wherein the head portion defines a head aperture configured to receive a dental instrument.

4. The assembly as recited in claim 1, wherein the actuation member includes side walls joined at an apex, a projection of the apex extending towards the distal end.

5. The assembly as recited in claim 4, wherein a cross-section of the actuation member defines a triangular geometry.

6. The assembly as recited in claim 5, wherein the at least two arm portions are integrally formed with the head portion such that surfaces of the at least two arm portions load against each other when the actuation member is located in a first position.

7. An assembly for expansion of tissue, comprising:
a head portion at a proximal end;
a pair of elongated arm portions extending between the head portion and a distal end, each of the pair of arm portions tapering towards the distal end to define a pointed engagement region operable to abut and pierce tissue;
wherein one or more apertures are defined in a thickness of each of the pair of arm portions, the one or more apertures dimensioned to receive tissue along a bone cavity defined in a jaw ridge; and
a wedge shaped actuation member moveable along a longitudinal axis extending between the proximal and distal ends to cause each of the pair of arm portions to pivot relative to the head portion, thereby spacing apart terminal ends of the pair of arm portions at the distal end such that the actuation member is axially spaced apart from the one or more apertures with respect to the longitudinal axis, the one or more apertures axially spaced apart from the engagement region with respect to the longitudinal axis.

8. The assembly as recited in claim 7, wherein each of the pair of arm portions slopes inwardly from the head portion to define an actuation cavity, the actuation member trapped in the actuation cavity.

9. The assembly as recited in claim 8, wherein the pair of arm portions are integrally formed with the head portion such that the pair of arm portions abut against surfaces of the actuation member.

10. A method of expanding bone tissue, comprising:
providing an assembly comprising:
   a body extending between proximal and distal ends, the body comprising:
      a head portion at the proximal end, and
      at least two arm portions extending between the head portion and the distal end to define an actuation cavity, each of the at least two arm portions tapering towards the distal end to define a pointed engagement region operable to abut and pierce tissue, and each of the at least two arm portions slopes inwardly from the head portion to define the actuation cavity; and
   an actuation member received in the actuation cavity, the actuation member moveable along a longitudinal axis to vary a distance between the at least two arm portions at the distal end, the longitudinal axis extending between the proximal and distal ends;
positioning the distal end of the assembly against cortical bone tissue of a jaw ride at a surgical site, the surgical site being a previous site of one or more teeth along the jaw ridge, and the jaw ridge being an alveolar ridge;
engaging the head portion to cause the distal end to pierce and move a distance through the cortical bone tissue to cause the cortical bone tissue to separate to define a bone cavity in the jaw ridge;
moving the actuation member relative to the at least two arm portions to cause the cortical bone tissue to further separate to widen the bone cavity, including spacing apart terminal ends of the at least two arm portions along the distal end with respect to the longitudinal axis;
positioning the assembly at the surgical site for a period time such that tissue thickness at the surgical site is increased and such that apertures receive an ingrowth of new bone tissue subsequent to the step of moving the actuation member, each of the apertures defined in a thickness of a respective one of the at least two arm portions such that the actuation member is axially spaced apart from the apertures with respect to the longitudinal axis during the period of time;
moving the actuation member to cause the at least two arm portions to abut against each other; and
removing the assembly from the bone tissue subsequent to receiving the ingrowth of new bone tissue within the apertures.

11. The method as recited in claim 10, comprising guiding a device through the head portion and between the at least two arm portions to engage bone tissue surrounding the bone cavity.

12. The assembly as recited in claim 6, wherein the aperture includes elongated slots defined in a respective arm portion of the at least two arm portions.

13. The assembly as recited in claim 9, wherein the one or more apertures include a first set of elongated slots and a second set of elongated slots defined in respective arm portions of the pair of arm portions.

14. The method as recited in claim 10, wherein the actuation member is axially spaced apart from the apertures with respect to the longitudinal axis during the step of positioning the assembly at the surgical site.

15. The method as recited in claim 10, wherein the actuation member includes side walls joined at an apex, a projection of the apex extends towards the distal end, a cross-section of the actuation member defines a triangular geometry, and the pair of arm portions are integrally formed with the head portion such that surfaces of the pair of arm portions load against each other during the step of positioning the distal end of the assembly.

16. The method as recited in claim 15, wherein the apertures include a first set of elongated slots and a second set of elongated slots defined in respective arm portions of the at least two arm portions.

17. The method as recited in claim 16, wherein the alveolar ridge is a horizontally atrophied alveolar ridge.

18. The method as recited in claim 17, wherein the step of moving the actuation member relative to the at least two arm portions is repeated over the period of time.

19. The method as recited in claim 18, wherein the step of positioning the assembly at the surgical site reducing the need for any bone-issue graft in the bone cavity.

20. The method as recited in claim 19, wherein the step of moving the actuation member relative to the at least two arm portions is performed subsequent to the apertures receiving the ingrowth of the new bone tissue.

* * * * *